US007761126B2

(12) United States Patent
Gardner et al.

(10) Patent No.: US 7,761,126 B2
(45) Date of Patent: *Jul. 20, 2010

(54) APPARATUS FOR NON-INVASIVE DETERMINATION OF DIRECTION AND RATE OF CHANGE OF AN ANALYTE

(75) Inventors: Craig M. Gardner, Arlington, MA (US); Trent D. Ridder, Sandia Park, NM (US); William Gruner, Albuquerque, NM (US)

(73) Assignee: Inlight Solutions, Inc., Albuquerque, NM (US)

( * ) Notice: Subject to any disclaimer, the term of this patent is extended or adjusted under 35 U.S.C. 154(b) by 1224 days.

This patent is subject to a terminal disclaimer.

(21) Appl. No.: 11/328,927

(22) Filed: Jan. 10, 2006

(65) Prior Publication Data

US 2006/0167349 A1  Jul. 27, 2006

Related U.S. Application Data (63) Continuation of application No. 10/753,506, filed on Jan. 8, 2004, now Pat. No. 7,016,713, which is a continuation-in-part of application No. 09/864,774, filed on May 24, 2001, now Pat. No. 6,718,189, which is a continuation of application No. 09/343,800, filed on Jun. 30, 1999, now Pat. No. 6,240,306, which is a continuation-in-part of application No. 09/174,812, filed on Oct. 19, 1998, now Pat. No. 6,152,876, which is a continuation-in-part of application No. 08/844,501, filed on Apr. 18, 1997, now Pat. No. 5,823,951, which is a continuation of application No. 08/512,940, filed on Aug. 9, 1995, now Pat. No. 5,655,530, application No. 11/328,927, which is a continuation-in-part of application No. 09/182,340, filed on Oct. 29, 1998, now Pat. No. 6,212,424.

(60) Provisional application No. 60/439,287, filed on Jan. 10, 2003.

(51) Int. Cl.
  *A61B 5/1455* (2006.01)
(52) U.S. Cl. .................. 600/310; 600/322; 600/316
(58) Field of Classification Search ................ 600/310, 600/316, 322
  See application file for complete search history.

(56) References Cited

U.S. PATENT DOCUMENTS

| 5,146,091 | A | * | 9/1992 | Knudson | 250/341.6 |
| 5,251,632 | A | * | 10/1993 | Delpy | 600/323 |
| 5,372,135 | A | * | 12/1994 | Mendelson et al. | 600/322 |
| 5,487,384 | A | * | 1/1996 | Lee | 600/316 |
| 5,507,288 | A | * | 4/1996 | Bocker et al. | 600/322 |
| 5,779,631 | A | * | 7/1998 | Chance | 600/328 |
| 5,978,691 | A | * | 11/1999 | Mills | 600/334 |

* cited by examiner

*Primary Examiner*—Eric F Winakur
*Assistant Examiner*—Etsub D Berhanu
(74) *Attorney, Agent, or Firm*—V. Gerald Grafe, Esq.

(57) ABSTRACT

The present invention relates generally to a non-invasive method and apparatus for measuring a fluid analyte, particularly relating to glucose or alcohol contained in blood or tissue, utilizing spectroscopic methods. More particularly, the method and apparatus incorporate means for detecting and quantifying changes in the concentration of specific analytes in tissue fluid. Also, the method and apparatus can be used to predict future levels of analyte concentration either in the tissue fluid or in blood in an adjacent vascular system.

19 Claims, 5 Drawing Sheets

APPARATUS FOR NON-INVASIVE DETERMINATION OF DIRECTION AND RATE OF CHANGE OF AN ANALYTE

CROSS REFERENCES TO RELATED APPLICATIONS

This application is a continuation of and claims priority under 35 U.S.C. §120 to U.S. patent application Ser. No. 10/753,506, entitled "Non-Invasive Determination of Direction And Rate Of Change of an Analyte," filed Jan. 8, 2004 now U.S. Pat. No. 7,016,713; which was a continuation-in-part of U.S. patent application Ser. No. 09/864,774, entitled "Method and Apparatus for Non-Invasive Blood Analyte Measurement with Fluid Compartment Equilibration," filed May 24, 2001 now U.S. Pat. No. 6,718,189, which was a continuation of application Ser. No. 09/343,800 filed Jun. 30. 1999 now U.S. Pat. No. 6,240,306, which was a Continuation-in-Part of U.S. patent application Ser. No. 09/174,812, filed Oct. 19, 1998 now U.S. Pat. No. 6,152,876 entitled "Method for Non-Invasive Blood Analyte Measurement with Improved Optical Interface", which is a Continuation-in-Part of U.S. patent application Ser. No. 08/844,501, filed Apr. 18, 1997, entitled "Method for Non-Invasive Blood Analyte Measurement with Improved Optical Interface", now U.S. Pat. No. 5,823,951, issued Oct. 20, 1998, which is a continuation of U.S. patent application Ser. No. 08/512,940, filed Aug. 9, 1995, now U.S. Pat. No. 5,655,530, issued Aug. 12, 1997, all to the same assignee as the present application; and was also a Continuation-in-Part of U.S. patent application Ser. No. 09/182,340, filed Oct. 29, 1998 now U.S. Pat. No. 6,212,424, entitled "Apparatus and Method for Determination of the Adequacy of Dialysis by Non-Invasive Near-Infrared Spectroscopy". The disclosure of each of the above referenced U.S. patent applications are expressly incorporated herein by reference. This application claims priority under 35 U.S.C. §119 to U.S. provisional application 60/439,287, "Determination of Direction And Rate Of Change of an Analyte," filed Jan. 10, 2003, the disclosure of which is incorporated herein by reference.

TECHNICAL FIELD

The present invention relates generally to a non-invasive method and apparatus for measuring a fluid analyte, particularly relating to glucose or alcohol as an analyte contained in blood or tissue, utilizing spectroscopic methods. More particularly, the method and apparatus incorporate means for detecting and quantifying changes in the concentration of specific analytes in tissue fluid. Also, the method and apparatus can be used to predict future levels of analyte concentration either in the tissue fluid or in blood in an adjacent vascular system. In addition, the changes in analyte concentration can be used to predict the analyte concentration in other tissue or blood compartments that are kinetically related to the compartment measured.

BACKGROUND OF THE INVENTION

The need and demand for an accurate, non-invasive method for determining blood glucose level in patients is well documented. Barnes et al. (U.S. Pat. No. 5,379,764) disclose the necessity for diabetics to frequently monitor glucose levels in their blood. It can be recognized that the more frequent the analysis, and the more analysis can accurately predict future glucose levels, the more readily large swings in glucose levels can be controlled or eliminated. These large swings are associated with the symptoms and complications of the disease, whose long-term effects can include heart disease, arteriosclerosis, blindness, stroke, hypertension, kidney failure, and premature death.

Presently, most home glucose monitoring is limited to methods and systems requiring a lancet cut into the finger. Repeated lancet cuts lead to repeated irritation and inconvenience, discouraging vigilant self-monitoring. This is believed so compromising to the diabetic patient that the most effective use of any form of diabetic management is rarely achieved.

Infrared spectroscopy is a generally known basis for analysis. In some forms, infrared spectroscopy measures the electromagnetic radiation (typical wavelengths in the range of 0.7-25 µm) a substance absorbs at various wavelengths, though other methods measure other effects a substance has on incident light. Absorption phenomena can include induced molecular vibrations and shifts in energy levels of individual atoms. Either phenomena causes the absorbing molecule or atom to switch to a higher energy state. These phenomena can be statistically shown to occur most frequently in limited ranges of wavelengths. Thus, for light passing through a substance at several wavelengths, the substance will absorb a greater percentage of photons at certain wavelengths than it will at others. The characterization of substances by their spectral absorption characteristics is well known.

At the molecular level, many primary vibrational states transitions occur in the mid-infrared wavelength region (i.e., wavelengths between 3-6 µm). However, non-invasive analyte detection in blood in this region is problematic, if not impossible, because water makes up the majority of the blood and demonstrates strong absorption characteristics at mid-infrared wavelengths. Typically, the problem is overcome through the use of shorter wavelengths that are not as strongly attenuated by water. Frequency overtones of the primary vibrational states exist at higher frequencies (thus shorter wavelengths), enabling quantitative determinations at these wavelengths.

It is known that glucose absorbs at multiple frequencies in both the mid- and near-infrared range. There are, however, other analytes in the blood which also absorb at similar frequencies. Due to the overlapping nature of these absorption bands, reliable non-invasive glucose measurement would be very difficult if only a single frequency were used for analysis. Analysis of spectral data for glucose measurement is facilitated by evaluation of absorption characteristics at several wavelengths, enabling the sensitivity, precision, accuracy, and reliability necessary for quantitative determination. Similar observations apply to other analytes such as urea and ethanol.

An additional difficulty can arise with respect to the incident power required to achieve a readable signal with respect to glucose levels. Glucose is a minor component by weight in blood, making high sensitivity an important aspect of design. One way to achieve higher sensitivity is to use a relatively large input power, which, however, can cause non-linearities in the optical systems themselves as well as in the material subjected to optical radiation. An alternative solution is to use measurements at several wavelengths and incorporate multivariate analysis techniques to statistically "filter out" data not related to the blood glucose concentration. Such techniques can be likewise applied to determine concentrations of other analytes, for example, constituents such as urea.

Many diabetic patients must lance themselves four to five times per day in order to measure their capillary blood glucose concentration and adjust insulin therapy and meals. Optical measurement provides an alternative means for measuring blood glucose by using the absorption or reflection spectra of tissue as a surrogate for the spectra of drawn blood. However, a problem encountered in non-invasive skin based measurements of standard medical blood analytes is the disparity between the concentration of a given analyte in the blood and the same analyte in the adjacent skin tissue water or interstitial fluid.

Blood, which, like tissue, is approximately 80% water, makes up less than 10% of the tissue volume. Since glucose is not made, but only disposed of, in skin, all of the glucose in the water that bathes cells (interstitial fluid) and that is inside cells comes from the blood vessels. That is, blood glucose must move out of the blood vessels and into the surrounding interstitial water and then into cellular elements. This effect is time dependent as well as dependent upon recent and present concentration gradients, the relative juxtaposition of compartments making up the tissue and the adjacent blood vessels, and the relative blood flow to the tissue. Thus, a measurement of total tissue glucose concentration is often very different from the concentration of glucose in the small blood vessels that make up a fraction of the total tissue volume.

Since glucose is only degraded in the skin (not manufactured), the interstitial space must be "filled" with glucose by the local blood vessels. As with any filling process, this is time dependent. Time lags between the concentration of glucose in interstitial fluid and blood have been documented ranging from 0 to 60 minutes, with an average lag of 20 minutes. Thus, the fact that the glucose must move between the tissue and blood causes errors in both interstitial space glucose and total tissue glucose concentration measurements when used as surrogates for blood glucose concentration measurements.

When measurements of total tissue or interstitial glucose concentration and blood glucose concentration are made concurrently, the two are correlated, but the tissue glucose concentrations lag behind the blood levels. Blood or serum glucose concentrations must be delayed in order to overlay the interstitial or total glucose concentration. When blood glucose concentration is changing rapidly (as might be expected in a diabetic after a meal high in sugars or after an insulin injection), the delay is more obvious and the difference between the blood glucose concentration and the other two measurements is most pronounced. Other analytes, such as ethanol, have similar tissue-blood kinetic behavior. The specific magnitude of the "lag" between the tissue and blood analyte concentrations is generally a function of the analyte's specific diffusion properties and each subject's physiology.

This presents obvious problems with respect to using the surrogate methods for monitoring and guiding therapy in diabetic patients. Given the concentration difference, determining whether a given technique is working based on infrequent, discrete measurements is believed impossible. Without more frequent measurements, it is difficult to determine whether the patient's blood glucose is in a steady state condition or is in flux.

The worst-case scenario in diabetic glucose management would be a quickly falling blood glucose concentration. Such a situation can result following a large insulin injection, unopposed by either glucose production in the liver or carbohydrate uptake from food in the digestive system. If a tissue measurement were made it would inappropriately report a level that is higher than the actual blood glucose concentration and that would not inform the patient of the quickly changing concentration. The patient would be unaware of their rapidly falling blood glucose level. The result of very low blood glucose concentrations (below 40 mg/dl, 2.2 mmol) is often loss of consciousness, coma and even brain damage or death if the patient is not discovered in time for medical intervention. For this reason, the ability to detect changing blood glucose levels is greatly desired.

Robinson et al. (U.S. Pat. No. 4,975,581) disclose a method and apparatus for measuring a characteristic of unknown value in a biological sample using infrared spectroscopy in conjunction with a multivariate model that is empirically derived from a set of spectra of biological samples of known characteristic values, and is incorporated herein by reference. The above-mentioned characteristic is generally the concentration of an analyte, such as glucose, but also can be any chemical or physical property of the sample. The method of Robinson et al. involves a two-step process that includes both calibration and prediction steps. In the calibration step, the infrared light is coupled to calibration samples of known characteristic values so that there is differential attenuation of at least several wavelengths of the infrared radiation as a function of the various components and analytes comprising the sample with known characteristic value. The infrared light is coupled to the sample by passing the light through the sample or by reflecting the light from the sample.

Absorption of the infrared light by the sample causes intensity variations of the detected (passed or backscattered) light that are a function of the wavelength. The resulting intensity variations at the at least several wavelengths are measured for the set of calibration samples of known characteristic values. Original or transformed intensity variations are then empirically related to the known characteristics of the calibration samples using a multivariate algorithm to obtain a multivariate calibration model. In the prediction step, the infrared light is coupled to a sample of unknown characteristic value, and the calibration model is applied to the original or transformed intensity variations of the appropriate wavelengths of light measured from this unknown sample. The result of the prediction step is the estimated value of the characteristic of the unknown sample.

Several of the embodiments disclosed by Robinson et al. are non-invasive and incorporate an optical interface having a sensor element. As depicted in FIGS. 5 and 6 of Robinson et al., the optical interface includes an input element and an output element. The input element is an infrared light source or near infrared light source. The input element interface with the sample or body portion containing blood to be tested includes transmitting the light energy or propagating the light energy to the surface of the skin via the air. The output element includes a detector which receives the transmitted or reflected light energy. The output interface with the sample also includes propagating the transmitted or reflected light through the air from the skin.

Robinson (U.S. Pat. No. 5,830,132) discloses a robust, accurate, non-invasive analyte monitor, and is also incorporated herein by reference. The method includes irradiating the tissue with infrared energy having at least several wavelengths in a given range of wavelengths so that there is differential absorption of at least some of the wavelengths by the tissue as a function of the wavelengths and the known characteristic, wherein the differential absorption causes intensity variations of the wavelengths incident from the tissue. The method further includes providing a first path through the tissue and a second path through the tissue, wherein the first path is optimized for a first sub-region of the range of wavelengths to maximize the differential absorption by at least some of the wavelengths in the first sub-region and then optimizing the second path for a second sub-region of the range to maximize the differential absorption by at least some of the wavelengths in the second sub-region. Robinson further discloses that the object of the invention is to measure blood analytes; therefore, maximizing the amount of blood in the tissue being irradiated is recognized as improving the measurement.

The accuracy of non-invasive measurement has historically been determined by its correlation to standard invasive blood measurements. To improve the stability and accuracy of the Robinson measurement, it is disclosed that sampling device should be thermostated so that the device does not act as a heat sink. It is further disclosed that the sampling device can be heated to an above normal tissue temperature to increase blood flow to the tissue area in contact with the device. The result is an increase in the vascular supply to the tissue and a corresponding increase in the blood content of the tissue. The end result of temperature regulation is taught as a reduction in spectral variation not associated with glucose and an improvement in measurement accuracy.

An additional problem exists with respect to measuring changing blood glucose levels. While a blood draw from within a blood vessel admittedly provides an intrusive, but accurate, measure of glucose concentration, a single blood draw might not indicate whether the glucose level, at the time of the draw, is constant, rising, or dropping. A second draw, occurring shortly after the first draw, can be used to determine whether the glucose concentration is changing, as well as the rate and direction of change. However, just like the first blood draw, the second blood draw would be another discomforting inconvenience; the additional discomfort and inconvenience can further discourage patient self-monitoring. Because, as explained above, information about the direction and rate of change of glucose concentration can be critical or at least useful information, it would be advantageous to provide a system for determining, non-invasively, the direction and rate of change of analyte concentrations in tissue and/or blood. Further, it would be useful to be able to use the measured analyte concentration and rate of change to determine the analyte's concentration in other, kinetically related, compartments.

Similar problems exist with regards to measurement of other analytes. As another example, the presence or concentration of alcohol can be determined noninvasively. As with glucose, the direction and rate of change of alcohol concentration can be important in many applications. For example, the rate of change can be useful in law enforcement situations where an officer administers an alcohol measurement to a person suspected of driving under the influence. In situations where the measured alcohol concentration is near, but below, the legal limit the officer may elect to allow the driver to continue to operate their vehicle. In this scenario, the person's alcohol could be increasing such that his or her blood alcohol will be above the legal limit in a matter of minutes. Current measurement methods cannot detect these circumstances. The alcohol rate of change measurement can alter the officer's decision by conveying that the persons alcohol concentration is near the legal limit and increasing. The officer could then detain the driver and perform a second measurement after a waiting period.

Accordingly, there is a need for an apparatus and method to determine whether analyte concentrations are rising, falling or at equilibrium along with an indication of the rate of change in order to optimize treatment. The present invention addresses these needs as well as other problems associated with existing methods for non-invasively measuring levels of and changes in analyte concentration in blood utilizing spectroscopy, and further applies to non-invasive measurements of analyte concentrations for other analytes and solutions.

SUMMARY OF THE INVENTION

The present invention includes methods and apparatuses for non-invasively measuring several characteristics of analyte concentrations in tissue. Some embodiments enable measurement of the value, rate of change, and direction of change of the analyte concentration by analyzing tissue. Several embodiments use spectroscopic techniques to achieve the non-invasive measurements, and can incorporate means for accelerating the equilibration of the concentrations of specific analytes between tissue compartments in a sample area to provide a present analysis or to amplifying the ability to monitor changes.

Several embodiments for non-invasively measuring the concentration of an analyte in blood include first providing an apparatus for measuring infrared absorption by an analyte-containing tissue. In some embodiments, the apparatus includes three main elements: an energy source, a sensor element, and a spectrum analyzer. The sensor element can include an input element and an output element. The input element can be operatively connected to the energy source by a first means for transmitting light, while the output element can be operatively connected to the spectrum analyzer by a second means for transmitting light.

In some embodiments, the input element and output element comprise lens systems that focus the light to and from the sample. In a preferred embodiment, the input element and output element comprise a single lens system that is utilized for both input of light from the energy source and output of both specular and diffusely reflected light from the analyte-containing sample. Alternatively, the input element and output element can comprise two lens systems, placed on opposing sides of an analyte-containing sample, wherein light from the energy source is transmitted to the input element and onto the sample, and light transmitted through the analyte-containing sample then passes through the output element to the spectrum analyzer.

The first means for transmitting light, in several embodiments, includes placing the energy source adjacent to the input element so that light from the source propagates through the air to the input element. The second means for transmitting light can include a single mirror or system of mirrors that direct the light energy exiting the output element through the air to the spectrum analyzer. Alternative embodiments can include using a transmission medium, such as glass, plastics or other materials, instead of air to prevent reflections or absorption in the air, or simply to provide a sealed, more robust system.

In practicing the method of the present invention, an analyte-containing tissue area is selected as the point of analysis. This area can include the skin surface on the finger, earlobe, forearm or any other skin surface. Preferably, the analyte-containing tissue in the area for sampling includes blood vessels near the surface and a relatively smooth, uncalloused skin surface. A preferred sample location is the underside of the forearm.

The sensor element is then placed so that the input element can direct input light incident upon the tissue surface. An index-matching medium, as suggested by Rohrscheib et al. in U.S. Pat. No. 6,240,306, can be used to improve the characteristics of the sensor element/tissue interface. The output element can be disposed on the same side of the sample tissue as the input element or it can be placed elsewhere, for example, on an opposite side. By these steps, the sensor element can be coupled to the analyte-containing tissue.

Once the sensor element is coupled to the analyte-containing tissue, the energy source is activated and the tissue is irradiated with light. The tissue surface will create specular reflections depending upon the mismatch between the refractive indices of the tissue surface and the medium through which the light propagates prior to incidence on the tissue surface. A greater mismatch of refractive indices will create a larger percentage of intensity reflection going back toward the input element. The tissue will absorb, diffract or reflect incident light according to the locations, concentrations, and spectral characteristics of the materials making up the tissue.

Depending upon the placement of the output element of the sensor element with respect to the placement of the input element and the tissue, the output element will either receive forward propagating light passing through the tissue or it can receive light that is scattered by some angle from the incident angle. The scattered light includes light that can backscatter from the tissue in the case of a sensor element having both the input and output elements on the same side of the tissue. The output element then transmits the light to a spectroscopic analyzer that will create a spectral analysis of the received light.

Before the output element can receive the light emanating from the tissue, the light exits the tissue and enter the output element. Again, there can be reflections at the interfaces of the tissue and any medium between the tissue and the output element. These reflections, along with diffraction and absorption by any medium between the tissue and the output element, can reduce the intensity received by the output element and, where light is not incident normally on one of the interfaces, can create problems of internal reflection.

The analyte concentration of the sample tissue can be at a different level than that of an adjacent vascular system. This different level of concentration will equilibrate over time as the analyte diffuses into fluids contained in the tissue. This disequilibrium between the tissue analyte concentration and the analyte concentration in the vascular system indicates a changing analyte concentration in the vascular system. The present invention is designed to detect a degree of disequilibrium in order to predict the direction and rate of change of glucose levels by, for example, taking two measurements at different times and determining the difference between the measurements.

In some embodiments of the present invention, it can be useful to accelerate the equilibration of the analyte concentrations in these separate tissue compartments. Such acceleration can improve the ability of the sensor element to detect, without requiring inordinately high sensitivity, a rate of change of the analyte concentration in the vascular system. In preferred embodiments, this acceleration toward equilibration is effected by causing an increase in vascular flow, for example, by applying localized heating of the tissue.

One problem that can arise is that the light received by the output element of the sensor can be dominated by specularly reflected light, which contains very little information regarding the analyte concentration inside the tissue. This specular light is largely noise, though it is possible that relative intensities of different wavelengths of the specular light can indicate a different effective index of refraction for the tissue for different wavelengths, which can in turn provide some indication of the surface composition of the tissue. However, in preferred applications of this method and system, the tissue surface will be skin, the actual surface of which is largely dead matter containing little information about the present analyte composition of the underlying tissue. Some embodiments incorporate a device for separating the specularly reflected light from the diffusely reflected light as suggested, for example, by Messerschmidt et al., in U.S. Pat. No. 5,636,633, which is incorporated herein by reference.

In a several embodiments, the concentration of glucose in the tissue is determined by first measuring the light intensity received by the output sensor as a function of wavelength. These measured intensities in combination with a calibration model are utilized by a multivariate algorithm to predict the glucose concentration in the tissue. The calibration model empirically relates the known glucose concentrations in a set of calibration samples to the measured intensity variations obtained from said calibration samples. In a preferred embodiment, the multivariate algorithm used is the partial least squares method, although other multivariate techniques can be employed. The predicted glucose concentration in the tissue can then be used to predict the concentration in adjacent blood vessels.

Analysis of the received data can also be used to predict the direction and rate at which blood glucose concentrations are changing. In some embodiments, multiple readings can be captured by the sensor element and compared to one another in order to determine the direction and rate of change of blood glucose concentrations. The speed at which change is taking place, in some embodiments, is used to predict a future value of blood glucose concentration. In other embodiments, the speed at which the change is taking place is used to predict the present concentration of the analyte in other compartments, such as blood. In several embodiments, the measurement of direction and rate of change of glucose concentration is enhanced by the use of an equilibration accelerating means, for example, localized heating, an applied rubrifractant, or an ingested or injected vasodilator.

These and various other advantages and features of novelty which characterize the present invention are pointed out with particularity in the claims annexed hereto and forming a part hereof. However, for a better understanding of the invention, its advantages, and the object obtained by its use, reference should be made to the drawings which form a further part hereof, and to the accompanying descriptive matter in which there are illustrated and described preferred embodiments of the present invention.

DETAILED DESCRIPTION OF THE INVENTION

Detailed embodiments of the present invention are disclosed herein. However, it is to be understood that the disclosed embodiments are merely exemplary of the present invention which can be embodied in various systems. Therefore, specific details disclosed herein are not to be interpreted as limiting, but rather as a basis for the claims and as a representative basis for teaching one of skill in the art to variously practice the invention. The invention makes use of signals, described in some of the examples as absorbance or other spectroscopic measurements. Signals can comprise any measurement obtained concerning the tissue, e.g., absorbance, reflectance, intensity of light returned, fluorescence, transmission, Raman spectra, all at one or more wavelengths; concentration of an analyte, and characteristics relating to change of any of the preceding. The invention also concerns analyte properties, where an analyte property can include, as examples, analyte concentration, presence of an analyte, identity of an analyte, change in analyte concentration, form of an analyte (e.g., oxygenation), temperature, activity, and conformation. Some embodiments make use of a model, where a model can be anything that relates a signal to the desired property, e.g., PLS models, linear regression models, Beer's law models. The invention also concerns tissue compartments, where a tissue compartment can be vascular or extra-vascular in nature. Venous, arterial, and capillary blood are examples of vascular compartments. Intra and extra-cellular fluid as well as interstitial fluid are examples of extra-vascular compartments.

The present invention is directed to a method for measurement of changing concentrations of tissue constituents using spectroscopy. A variety of techniques for enhancing the characteristics of measured spectra have been uncovered, and some of these are included in the various illustrative embodiments below to demonstrate their use. The inclusion of details such as heating elements, rubrifractants, and index-matching media should not be interpreted as limiting the present invention to these particular forms of enhancement or equilibration. These enhancements are not required to practice the present invention, but are included for illustrative purposes only.

It has been found that a sample such as human tissue can be a complex matrix of materials with differing refractive indices and absorption properties. One material of interest which is used to explain the embodiments here is glucose. However, the illustration of embodiments herein that relies on glucose should not be considered limiting, as the present invention is suitable for measuring many analytes, whether in the blood, interstitial tissue, or other bodily media. For example, the present invention is suitable for measuring changing concentrations of urea in blood, as described by Robinson et al. in U.S. Pat. No. 6,212,424, which is expressly incorporated herein by reference. It is also suitable for measuring changing concentrations of alcohol in tissue. Primarily for purposes of illustration, not limitation, the present invention is described with particular reference to blood glucose measurements.

The present invention, in some embodiments, monitors the spectral patterns of reflection and/or absorption of tissue over a period of time in order to determine a rate and direction of change of concentration of one or more analytes in either the tissue or in an adjacent vasculature, for example, in blood supplying the tissue. In most systems of interest, where a supporting vasculature contains liquid having an analyte concentration that is different from surrounding tissue, the analyte concentration of the tissue will change towards a condition of equilibrium. In some embodiments of the present invention, ordinary mechanisms of equilibration of the body, tissue and vasculature (such as simple diffusion) can be relied upon to change the tissue analyte concentration and provide a basis for predicting the rate of change of analyte concentrations within the vasculature or blood.

In one embodiment, equilibration accelerators are used to speed the process of equilibration. Through the use of equilibration accelerators, such as applied heat, rubrifactants, vasodilators, and other chemicals or conditions, the measurable spectral properties of the tissue will be urged to change more quickly or, more descriptively, more dramatically in a shorter period of time. It is proposed that by accelerating the process towards equilibration, the accuracy of measurements of the present invention can be enhanced without requiring more sensitive spectroscopic equipment. In short, where it can be necessary to quantify a change of a fraction of a percent over a relatively long time period without equilibration accelerants, more sensitive (and possibly less durable and more expensive) equipment can be needed to provide accurate analysis. In contrast, with equilibration accelerants, less sensitive equipment can provide adequate accuracy. Further, with equilibration accelerants, the period of time over which a measurement must be made, or the number of samples required, can also be reduced. While the use of accelerants can aid the determination of the rate of concentration change, they are not required for the subsequent use of the rate in corrective steps.

The topic of accelerating equilibration is discussed in detail by Rohrscheib et al. in U.S. Pat. No. 6,240,306, which is expressly incorporated herein by reference. The methods, equipment and chemicals or drugs discussed therein can be used as accelerants with the present invention. Some such chemicals include nicotinic acid, methyl nicotinamide, minoxidil, nitroglycerin, histamine, capsaicin, or menthol which, when applied, increase local dermal blood flow equivalent to that induced by heating. One of the aspects that is important with respect to the present invention is correct characterization of the effects of the equilibrium accelerant used. It is proposed that certain accelerants can cause different forms or rates of equilibration. Thus, in order to provide accurate analysis of the changes in analyte concentration being measured, information about the equilibration accelerant used should be known as well.

One of the simpler equilibrium accelerants is applied heat. In preferred near-infrared measurement devices of the present invention, infrared energy is coupled into the skin via optical lenses, and, as part of this embodiment, the lens is maintained at a desired temperature. The lens itself heats the local tissue in order to increase the blood flow and thereby accelerate equilibration. The lens mount can contain the heating elements and temperature sensor that maintain the lens and local arm at the desired temperature. In a preferred embodiment, the incident light beam and the reflected infrared energy beams pass through the same heated lens; such a system is displayed below in FIG. 1.

The average core body temperature of a human is 38° C., and the average skin temperature of a human is 35° C. Thus, if heat is utilized to increase blood flow, enhanced equilibration begins as soon as the skin temperature rises above 35° C. Preferably, the skin temperature is allowed to rise about 5° C., and more preferably about 7° C. Assuming a heat source temperature of about 40° C. to 42° C., equilibration begins almost immediately upon contact (i.e., heat transfer) with the tissue, and full temperature stabilization of tissue water occurs at about 3 to 4 minutes thereafter. During this time the spectra of the tissue can be changing. In some embodiments, monitoring changes during the time of accelerated equilibration allows prediction of the direction and rate of change of analyte concentration to be more easily predicted. In another preferred embodiment, a future concentration for the analyte in blood can also be predicted. In other embodiments, the analyte concentration of kinetically related tissue compartments, such as blood, can be predicted.

The infrared source also acts to heat the tissue and is considered one preferred equilibrium accelerant with separate heating. Due to natural changes from simple diffusion and heat from the infrared source, direction and rate of change can be accurately determined from multiple spectroscopic samples over a period of time.

Alternatively, if a rubrifractant is utilized to cause the increase in blood flow, the effect on equilibration depends on the vasodilating characteristics of the particular rubrifractant selected. Of course, the effect on equilibration also depends on the particular tissue characteristics and physiological characteristics of the test subject, which vary from person to person.

It has been found that using a means for equilibrating the glucose or analyte concentration between the vascular system and the tissue allows a direction and rate of change of analyte concentration measurement to be made more quickly and accurately. Using, for illustration, the underside of the forearm as a location for testing to take place, a heated surface can be used to warm the arm. When the arm is placed in contact with a heated surface, the external surface of the skin, the epidermis, rapidly equilibrates temperature-wise with the heated surface. The transfer of heat into the deeper tissue areas, however, takes a finite period of time. Thus, there is a delay before the interstitial water becomes fully equilibrated. Monitoring the changing spectral characteristics of the tissue during this delay gives an indication of the rate at which analyte concentration is changing. The faster equilibration occurs, the less time is required to encounter a detectable amount of change in spectral characteristics, if such a change is forthcoming. If the blood glucose levels are not changing significantly, it can occur that no change in spectral characteristics can be sensed, since the tissue and blood can already be at or near equilibrium.

To determine the delay between placement of the arm in contact with a heated surface during optical sampling and increased temperature of the tissue water, an experiment was conducted. An unheated arm was placed in contact with a tissue sampling device controlled to a temperature of 40° C. A near infrared model for predicting tissue water temperature was applied to the resulting spectra. The study was repeated on three subjects. The results of the spectroscopic analysis for the prediction of tissue water temperature showed the tissue water reached greater than 90% equilibration with the temperature of the heating plate in less than 4 minutes. It was noted that there is time to equilibration differences between the patients tested. It was also noted that the near infrared light penetrating the tissue also contributes to heating of tissue water due to absorption.

In analyzing for an analyte in tissue, measurements can be made in at least two different modes. It is recognized that one can measure light transmitted through a section of tissue, or one can measure light reflected or remitted from tissue. It has been recognized that transmission is the preferred method of analysis in spectroscopy because of the forward scattering of light as it passes through the tissue. However, it is difficult to find a part of the body which is optically thin enough to pass near infrared light through, especially at the longer wavelengths, while also providing sufficient blood flow to allow accurate measurements. Thus, a preferred method for measurement in the present invention is to focus on the reflectance of light from the sample.

Photons reflect and refract at refractive index discontinuities, and so light impinging on tissue immediately has a small reflectance at the tissue surface, particularly where the light passes from air (index n~1) into tissue (index n~1.4). This is referred to as specular reflectance. Since this light does not penetrate into the tissue, it contains little information about the tissue constituents. While in tissue, light is refracted at a plethora of index discontinuities including, for example, cell walls. For both back-scattered light measurements and forward propagating measurements, this scattering results in photon incidence at boundaries from tissue into air which deviated from normal incidence. The passage from a medium having a higher index to a medium having a lower index results in the phenomenon of internal reflection. Internal reflection occurs when incident angle deviates from normal by too great an amount (called the critical angle), and the photon does not pass the interface but is instead reflected back into the medium having a higher index of refraction.

Both specular reflection and internal reflection are sources of loss for the present invention. Applicants have determined that one way to reduce the effects of these reflections is to include an index matching medium between the optical elements (the input device inputting light onto the tissue and the output device receiving the backscattered or forward-propagating light, depending upon the configuration) and the sample tissue. Such an index matching medium can improve the interface characteristics of the present invention, but this improvement, while beneficial, is not required to practice the present invention.

Figure 1:
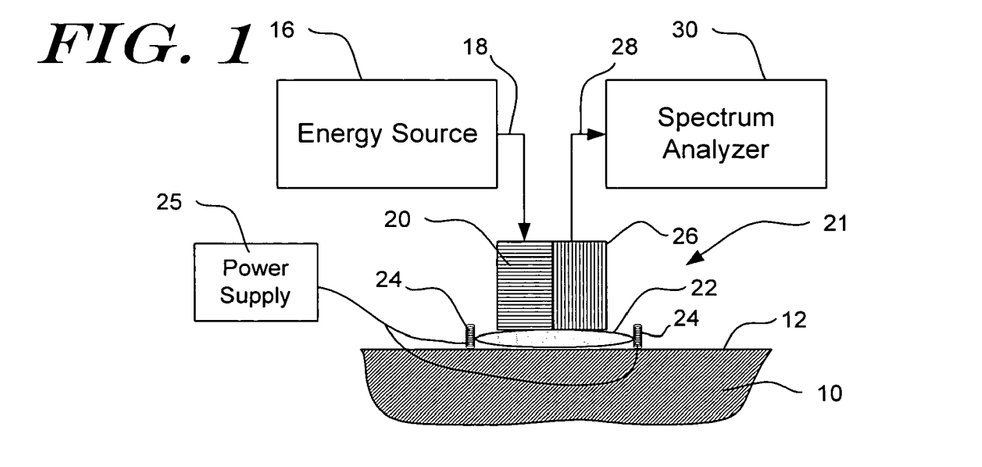
FIG. 1 is a partial cross-sectional view of a sensor element coupled to a tissue surface including a heating element.
Figure 2:
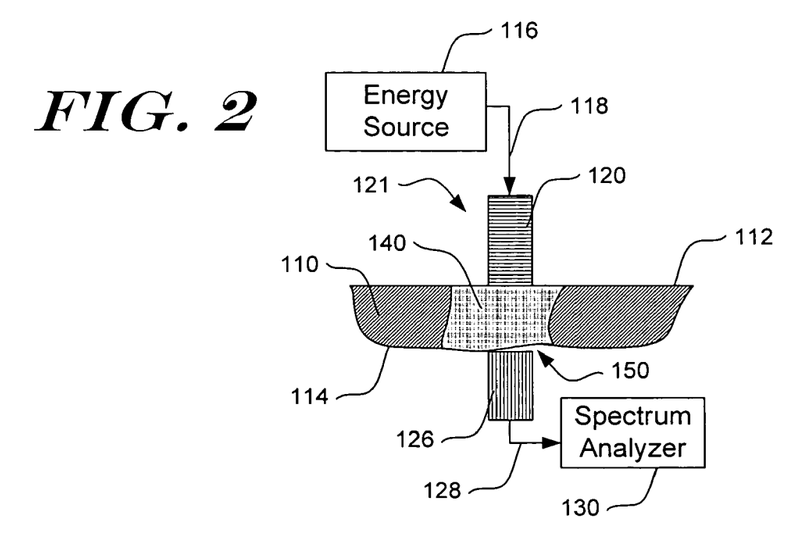
FIG. 2 is a partial cross-sectional view of an alternative embodiment of a sensor element coupled to opposite sides of a tissue sample with a chemical accelerant applied to the tissue.

Now referring to FIGS. 1 and 2, partial cross-sectional views of two embodiments of an apparatus for non-invasively measuring a blood analyte concentration are depicted. The relative size, shape and detail of physical components are not depicted. The system is depicted in simplified form recognizing that a complete system includes many components not depicted. One such system is disclosed in co-pending U.S. patent application Ser. No. 09/832,585, entitled "System for Non-Invasive Measurement of Glucose in Humans," filed Apr. 11, 2001, the disclosure of which is incorporated herein by reference.

The apparatus depicted in FIG. 1 includes an energy source 16. The energy source 16 is coupled by a first optical transmission means 18 to an input element 20 that is part of the sensor element 21. The sensor element 21 also includes a lens 22, heating elements 24 and an output element 26. The lens 22 is placed adjacent the surface 12 of tissue sample 10. The output element is coupled by a second optical transmission means 28 to the spectrum analyzer 30. The illustrative embodiment of FIG. 1 operates as follows:

The energy source 16 produces near infrared light and couples the light into first optical transmission means 18, which transmits the light to the input element 20. The input element 20 couples the light into lens 22, which then passes the light onto the surface 12 of tissue 10. In order to accelerate the equilibration of tissue 10 with its adjacent vasculature (not shown), the lens 22 is heated with heating elements 24. Heating elements 24 are depicted in the illustrative embodiment of FIG. 1 as small coils, however, a multitude of alternative heat sources can also be used as well. The apparatus can include a separate power supply 25 for the heating elements 24, or, alternatively, the energy source 16 can provide the heat energy itself, or can be connected to the heating elements 24 to power them. Because the lens 22 is in contact with the surface 12, the tissue 10 can be heated.

Light reflected back, either from the surface 12 or through internal reflections in the tissue 10, can be coupled via the lens into the output element 26. Specular light, which reflects from the surface 12, can be filtered by devices or methods for eliminating specular light, such as that of Messerschmidt, et al., noted above. The output element 26 then couples the light into a second optical transmission means 28 which passes the light on to the spectrum analyzer 30.

In one embodiment, the energy source 16 begins producing near infrared light before the heating elements 24 begin heating the lens 22 and hence the tissue 10. Then, the heating elements 24 begin supplying heat to the lens 22 and the tissue 10. While the tissue is heated, the spectrum analyzer 30 samples the reflected light spectra. If the concentration of the measured analyte in the tissue 10 is changing, the spectrum analyzer 30 will receive changing spectra during the time that the tissue 10 is equilibrating. Alternatively, the infrared source provides sufficient heating to accelerate equilibration. If no heating or other equilibration accelerant were provided, the time during which equilibration takes place would be higher, and the spectra sampled by the spectrum analyzer 30 would change less per unit time during equilibration, but still can provide sufficient information for detection of rate-of-change and direction-of-change due to natural processes in the tissue.

Figure 4:
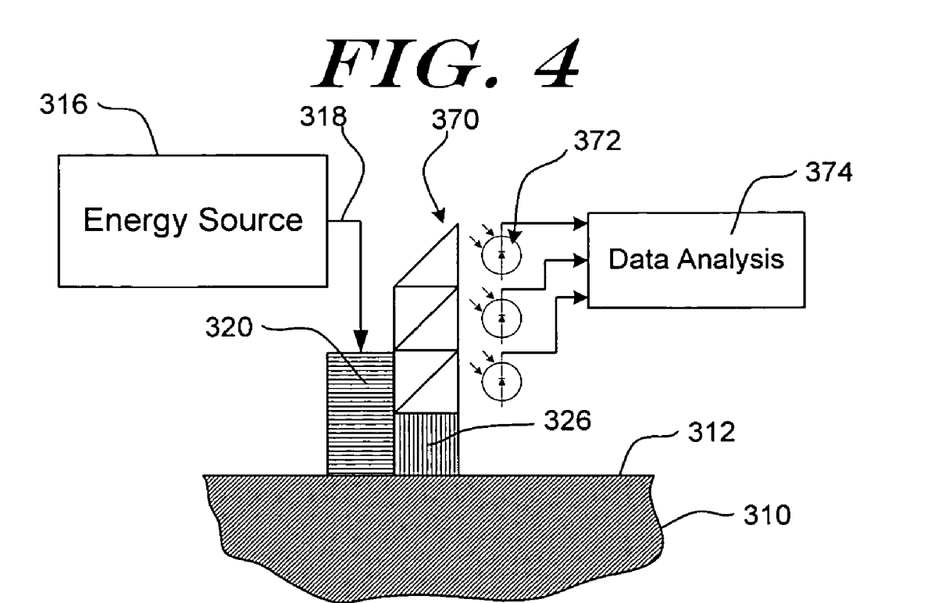
FIG. 4 is a partial cross-sectional view of an alternative embodiment with a sensor element coupled to a tissue surface using an alternative output element.

In another embodiment, the second optical transmission means 28 can be replaced by an electrical transmission means, and the optical energy received by the output element 26 would be received by photoreceptors, such as photodiodes. The output of the photoreceptors would then be coupled into a data analyzer that can replace the spectrum analyzer 30. In short, the alternative embodiment would place the spectrum analyzer immediately following the lens 22. Another alternative embodiment building on this possibility is shown in FIG. 4 and explained below.

The energy source 16 is preferably a wide band, infrared black body source. Other sources can certainly be used, including but not limited to a variety of lasers including semiconductor lasers and vertical cavity surface emitting lasers, as well as light emitting diodes or arrays of lasers or light emitting diodes. In some embodiments, the optical wavelengths emitted from the energy source 16 are between 0.7 and 3.0 μm. The first and second optical transmission means 18, 28 can be any means suitable for transmitting light, for example, simple passage through air, optical fibers, waveguides or other media that might or might not include beam shaping or confinement structures. Either of the transmission means can also include wavelength selective devices for eliminating unneeded, undesired, potentially harmful, or possibly interfering bands of light. Further, the optical transmission means 18, 28 can include devices enabling a user to determine whether or not the energy source is properly working.

As shown in FIG. 1, the input element 20 and output element 26 both use an optical lens 22 for coupling light into the tissue 10. However, it is understood that other beam focusing means can be utilized in conjunction with or as alternatives to the optical lens to alter the area of illumination. For example, a multiple lens system, tapered fibers, or other conventional optical beam-shaping devices can be utilized to alter the input light energy. Alternatively, systems using highly directional sources, such as lasers, can function without the need for additional focusing elements.

FIG. 2 shows another embodiment of the present invention. The overall system is similar to that shown in FIG. 1. In the illustrative embodiment shown in FIG. 2, the energy source 116 produces near-infrared light, which is coupled into first optical transmission means 118 and then into input means 120. Input means 120 can provide some beam shaping or other functionality as it then couples the light onto the first surface 112 of tissue 110. The tissue 110 has been treated with a rubrifactant lotion including a dye for changing the appearance of first surface 112, as shown at 140. Such a dye can be included to enable the user to determine where the lotion has been applied and whether coverage is adequate. Also, such a dye can be used to verify system function as discussed in co-pending U.S. patent application Ser. No. 10/410,006, entitled "Reduction of Errors in Non-Invasive Tissue Sampling," the disclosure of which is incorporated herein by reference. The rubrifactant is included as an equilibration accelerant, causing increased blood flow to the tissue 110 in the area in which it is applied 140.

An output means 126 is coupled to second surface 114 of tissue 110. As shown in FIG. 2, second surface 114 is on an opposing side of tissue 110 from first surface 112. Therefore, the light captured by output element 126 will be light that is transmitted through the tissue 110. After the transmitted light is captured by the output means 126, it is transmitted through second optical transmission means 128 to the spectrum analyzer 130. A notable difference between the illustrative embodiments of FIGS. 1 and 2 is that, while in FIG. 1 the reflected or backscattered light is captured and analyzed, the illustrative embodiment of FIG. 2 measures the forward scattered light that passes through the tissue sample 110.

A potential source of error for a non-invasive measurement system is also illustrated in FIG. 2. Where the second surface 114 of tissue 110 meets output element 126, there is a gap 150. Such gaps can occur for a variety of reasons, for example, as a result of air trapped between the surface 114 and the output element 126, or roughness of the surface 114. The gap 150 leads to a spatially inconsistent interface, and can cause erroneous measurements to result. A particular problem would occur if the interface of the output element 126 has a high index of refraction, which would result in significant reflection from the air-output element 126 interface. For an interface from $n_1$ to $n_2$, the reflectance is:

$$R = \left(\frac{n_1 - n_2}{n_1 + n_2}\right)^2$$

Thus there is the potential for the gap to introduce a loss of coupled power, reducing the effectiveness of the system.

Figure 3:
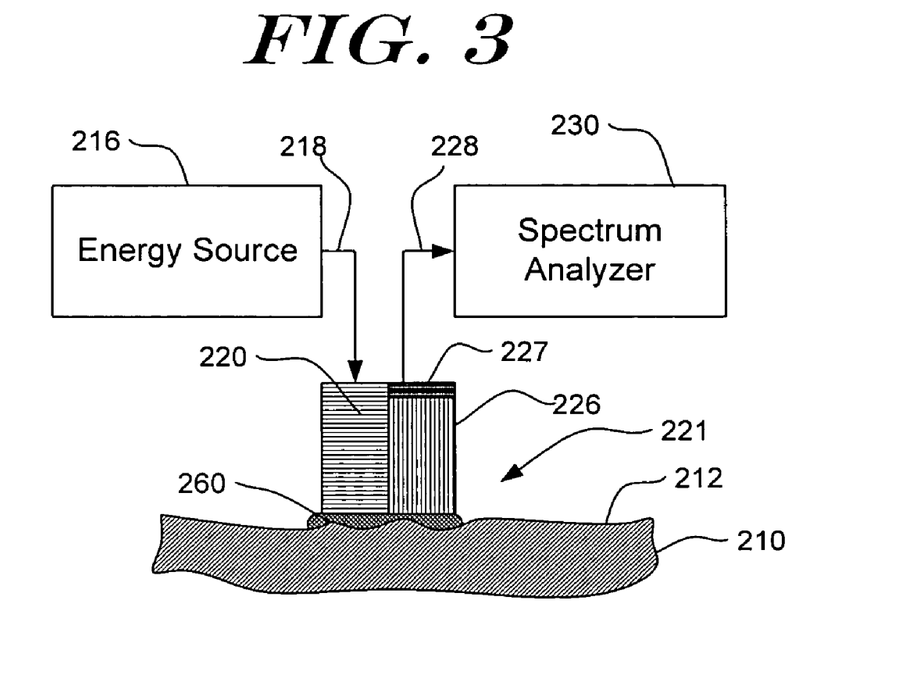
FIG. 3 is a partial cross-sectional view of a sensor element coupled to a tissue surface via an index matching substance.

One method for reducing the potential for gaps and reducing the effects of reflections at the interfaces between tissue and input/output element is illustrated in the embodiment shown in FIG. 3. In the illustrative embodiment of FIG. 3, an energy source 216 is again coupled via first optical coupling means 218 to an input element 220. As shown in FIG. 3, the tissue 210 has an irregular surface 212. An interface enhancing substance 260 has been applied to act as a medium between the input element 220 and the tissue 210. In some embodiments, interface enhancing substance 260 is an index matching medium, matching the indices of refraction of the tissue surface 212 and the interface surfaces of both the input element 220 as well as the output element 226 (note that this also entails selecting such interface surfaces to match the index of refraction of the tissue surface 212). The matched indices of refraction will assure a very small reflectance at the interfaces of the tissue 210 and the interface enhancing substance 260 as well as between the interfaces of the input/output elements 220, 226 and the interface enhancing substance 260.

The light coupled to the input element 220 is thus passed through the interface enhancing substance 260 onto the surface 212 of the tissue 210. Light which reflects from within the tissue 210 then passes out through the interface enhancing substance 260 to the output element 226. The output element 226 couples the light into the second optical transmission means 228, which passes the light to the spectrum analyzer 230.

FIG. 3 also includes an illustrative embodiment of the sensor 221 including, as part of the output element 226, an optical shutter 227. The shutter 227 modulates the signal leaving the output element 226 by selectively opening and closing. The shutter 227 is purely illustrative, and can easily be replaced by a variety of devices in a variety of locations, for example, the shutter 227 can be part of the spectrum analyzer 230, or the physical device can be eliminated and the function of modulation can be performed by electronics controlling analysis in the spectrum analyzer 230. Further, the shutter 227 can be used to modulate the output light, as shown, or it can be used to modulate the light incident on tissue 210. The shutter 227 can be a physically moving device, or can be chosen from a variety of modulation devices, for example, electro-optic or acousto-optic modulators as are known to those skilled in the optical arts.

FIG. 4 shows a further illustrative embodiment of the present invention. In the embodiment shown in FIG. 4, the separate spectrum analyzer shown in earlier figures is replaced by other elements that perform a similar function. As shown in FIG. 4, an energy source 316 produces optical radiation, which is coupled into optical transmission means 318 into input element 320. The input element 320 couples the radiation into the tissue 310 through surface 312. An output element 326 is shown, also coupled to tissue 310 through surface 312. Rather than transmitting the exiting light to a separate spectrum analyzer, the output element 326 couples the light to an array of beam splitting devices 370. The beam splitting devices then direct the light onto an array of photoreceptors 372. The output of the elements in the array of photoreceptors 372 is coupled to a data analysis block 374.

In the illustrative embodiment of FIG. 4, the array of photoreceptors 372 is shown as an array of photodiodes. Devices other than photodiodes can be used, for example, an array of microbolometers can be used to receive the output light. One skilled in the optical arts can readily identify a variety of different means for detecting the amplitude of light received at certain wavelengths by the array of photoreceptors 372. For example, the array of beam splitting devices 370 shown might not be wavelength selective, but either reflects or transmits a certain percentage of incident power. Additional filters or optical devices can be included to filter the light passed to the elements of the photoreceptor array 372, with such filters appearing as part of the array of beam splitting devices. Another method would be to pass the light from output element 326 into a prism that would spatially divide the light by wavelength, and the photoreceptor array 372 can be spatially arranged to match certain parts of the optical spectrum. Thus, each element of the photoreceptor array 372 can be subjected to a narrow bandwidth of output light.

The discussion now returns to FIG. 1, which shows use of a heating element 24 to warm lens 22 and hence tissue 10. During actual use of a non-invasive apparatus of the present invention, Applicants have found that the surface of a patient's arm or sample area on such arm will be approximately at room temperature. For clarity, the room temperature arm will be called a "cold arm". If the cold arm is placed in the optical sampling device of the present invention and heated to accelerate equilibration, the concentration difference between the blood (a first tissue compartment) and tissue (a second tissue compartment) will decrease over time due to the improved exchange between these two tissue compartments. In simple terms, a cold arm glucose measurement by the infrared non-invasive method and apparatus of the present invention will generate a glucose or other analyte measurement that is representative of past blood glucose or analyte levels. As the arm warms up and the blood and tissue glucose or other analyte levels are allowed to equilibrate, the non-invasive measurement will represent current blood glucose levels.

Because the cold arm represents a past blood glucose level, both the direction and rate of change of blood glucose or other analyte can be determined. Thus, Applicants have found that within a single measurement sitting much information can be gathered in a short period of time. This information includes the direction of glucose or other analyte change, the rate of change over the preceding period, and the absolute glucose concentration in the blood upon reaching equilibrium. Of important note is the fact that such a reading of the rate and direction of analyte concentration would require multiple blood draws using conventional technology.

In a preferred method, the patient's cold arm is placed in the non-invasive measurement device. The monitor would then make a non-invasive measurement during the insertion period. If the patient is at a stable analyte concentration, the non-invasive analyte reading would be relatively constant during the equilibration period. For example, the readings over the first three minutes would be approximately the same. However, if the patient's glucose or other analyte was changing rapidly, or had been changing rapidly before the insertion, the non-invasive measurements would change rapidly over time due to the equilibration between the tissue and the blood during the equilibration period. During a period of increasing blood glucose concentration, the test measurement on the cold arm would generate a reading that would be actually below the blood value. As the arm equilibrates the blood and tissue glucose values equilibrate. Multiple non-invasive tissue measurements can be made during a single sitting to monitor both the absolute magnitude and the rate of change in magnitude of the total tissue analyte measurement.

In contrast to a period of increasing blood analyte concentration or glucose concentration, a period of decreasing concentration would be indicated by a higher glucose concentration in the tissue than that in the blood. Thus, the non-invasive prediction of the cold arm would be above the actual blood concentration. This disequilibrium would be indicated upon activation of the means for equilibrating concentrations within tissue compartments and commensurate rapid decrease in the total tissue analyte concentration as equilibrium is achieved.

The arm, in its native state, will exhibit disequilibrium between tissue and blood glucose concentrations when the glucose concentration is changing. A non-invasive measurement under conditions of disequilibrium will provide information about past blood glucose concentrations. As the condition of disequilibrium is reduced, the non-invasive measurement becomes a measurement of current blood glucose concentration. In several embodiments, measurements are made under a condition of disequilibrium and, if a patient's glucose has been changing, the non-invasive device can provide information regarding both the direction and rate of change of the patient's glucose or other analyte concentration. With this information, an accurate prediction of future levels can be made and treatment can be made in response to the information.

Figure 5:
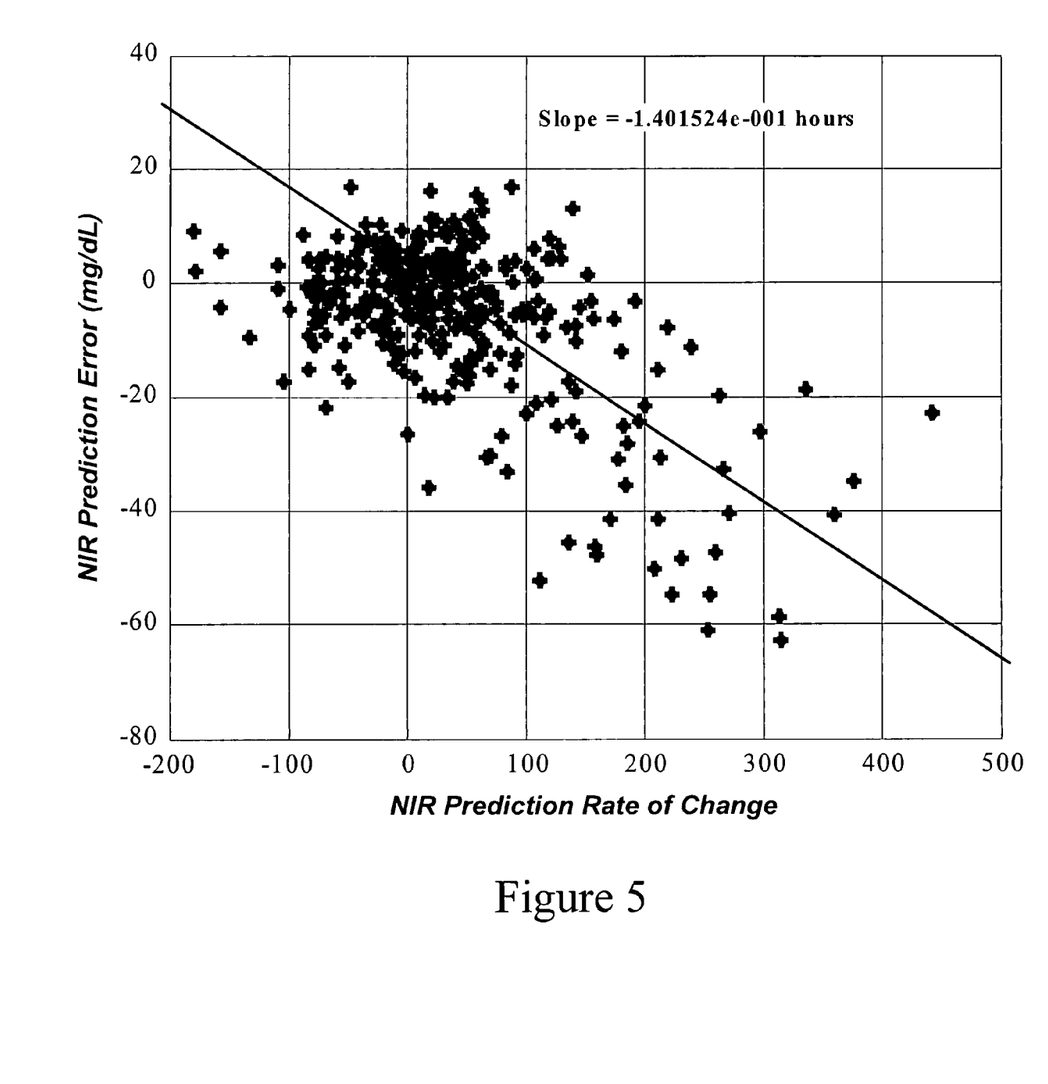
FIG. 5 is a plot that demonstrates the relationship between noninvasive prediction error relative to blood and the noninvasive prediction rate of change.
Figure 6:
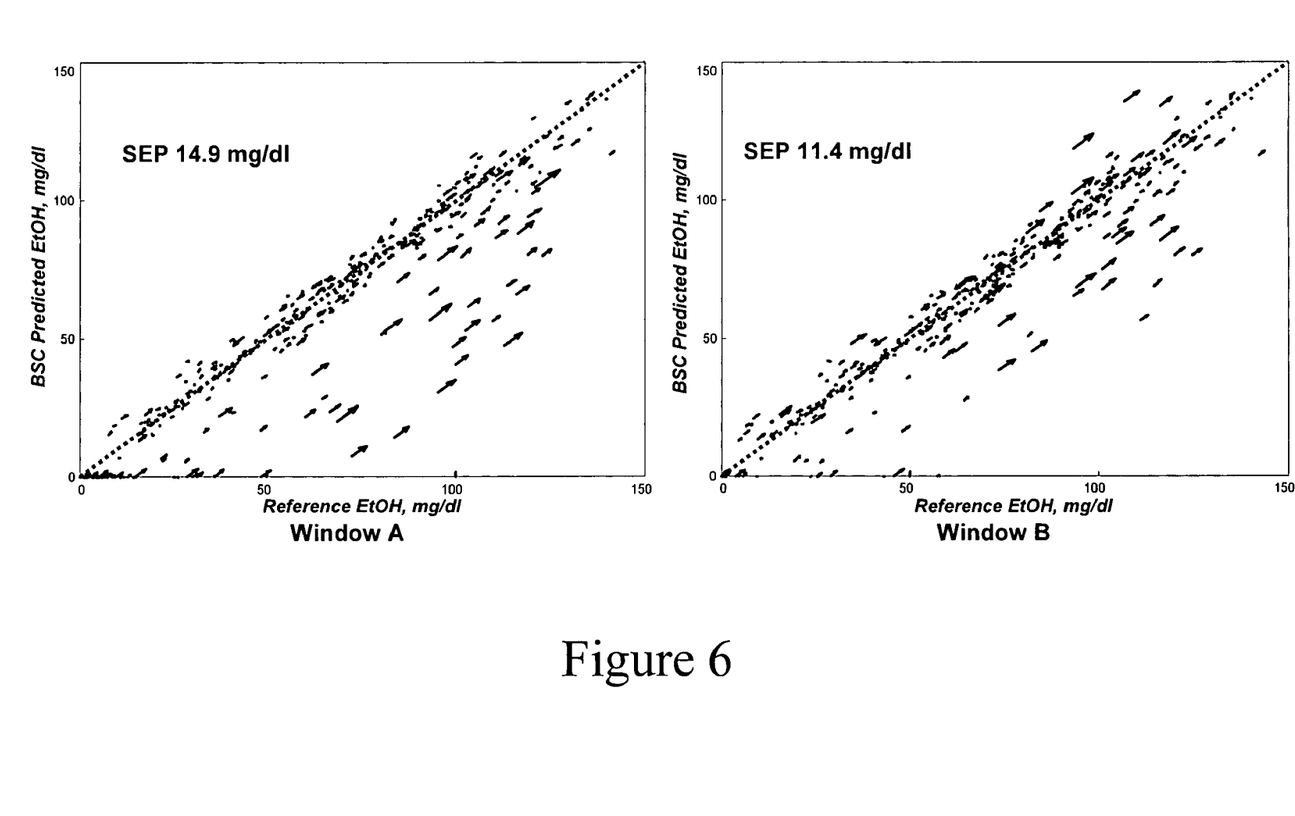
FIG. 6 is a plot that shows the near infrared predictions versus contemporaneous blood measurements before and after rate correction.

The analyte concentration and its rate of change can be used to determine the concentration of the analyte in another tissue compartment. An example embodiment consists of establishing a relationship between the prediction rate of change and the concentration of the analyte in a kinetically related compartment. FIG. 5 is a plot of noninvasive ethanol prediction error relative to blood ethanol versus the noninvasive prediction rate of change. The significant correlation between the prediction error and prediction rate of change indicates that prediction error increases as the magnitude of the prediction rate of change increases. The slope of the regression line in FIG. 5 can be used to determine a correction value for subsequent measurements. This correction can be implemented by using the equation of the regression line and a measurement's prediction rate of change in order to determine the expected prediction error of the measurement relative to blood. The expected prediction error is then added to the prediction in order to provide a measurement of the blood concentration. FIG. 6 shows quiver plots of the ethanol predictions versus contemporaneous reference blood alcohol concentration before and after the correction. The location of each arrow in FIG. 6 represents the value of the ethanol prediction. The direction and length of each arrow represent the direction and magnitude of the rate of change of the prediction. Comparison of the two windows in FIG. 6 shows that the correction has a stronger effect on the largest arrows.

Figure 7:
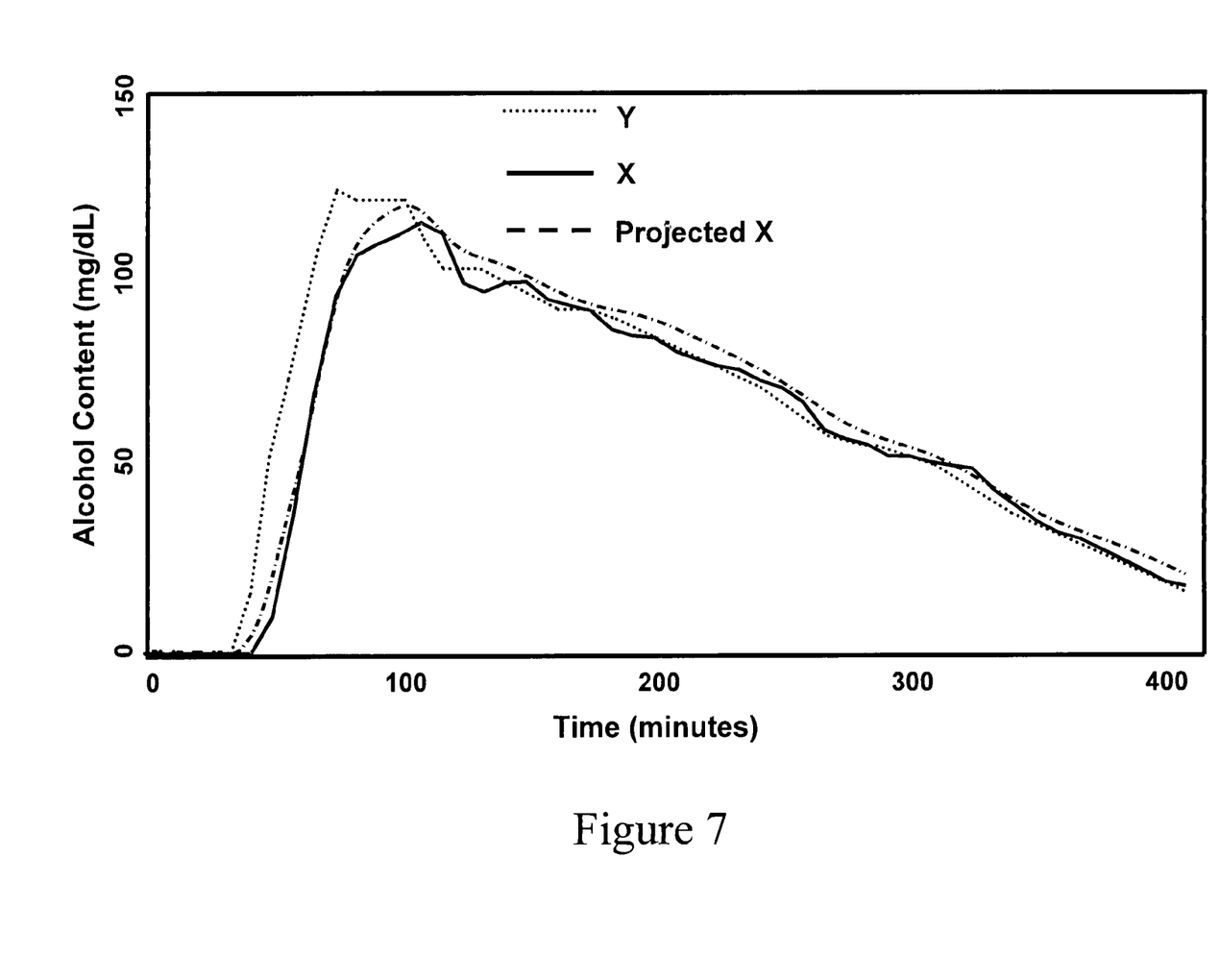
FIG. 7 is a plot of analyte concentrations over time for two different tissue compartments that are kinetically related by a first order diffusion model and the projection of the concentration of one compartment using the known concentrations from the other and the diffusion equation.

The relationship between the prediction rate of change and the analyte concentration in another compartment can be established using a known or experimentally determined equation. For example, a single parameter diffusion model has been shown to explain the kinetic relationship between tissue and blood analyte concentration. See, e.g., D. Shmidtke, A. Freeland, A. Heller, R. Bonnecaze, "Measurement and modeling of the transient difference between blood and subcutaneous glucose concentrations in the rat after injection of insulin", Proc. Natl. Acad. Sci. USA, 95, 294 (1998). The equation for a first order diffusion system is $$\frac{dY}{dt} = k(X - Y)$$

where X is the concentration of the analyte in one compartment, Y is the concentration in a second compartment, k is the diffusion constant, and dY/dt is the rate of change of Y. The diffusion equation can be rewritten in terms of Y, its rate of change, and the diffusion constant. Thus, knowledge of the value of Y, its rate of change, and the diffusion constant allows direct calculation of the value of X at the same moment in time. FIG. 7 is an example of this process that shows the analyte concentrations over time (X and Y) for two tissue compartments. The third trace is the projection of X using Y, the rate of change of Y, the first order diffusion system equation, and an estimated diffusion constant. The agreement between X and projected X indicates that knowledge of Y, its rate of change, and the diffusion constant is sufficient to allow the estimation of an analyte concentrations in other tissue compartments. The above examples are meant to be illustrative of the use of the prediction rate of change as a correction methodology for the kinetic mismatch in analyte concentration between two tissue compartments.

Prior to analyte testing on tissue, a variety of surface preparation agents can be used. For example, hydrophilic substances, such as isopropyl alcohol, can be used to pull away moisture in the tissue surface, reducing the effects of water on the incident light. Alternatively, a surfactant can be used to increase surface moisture to allow for better contact between the tissue surface and either an index-matching medium or the light input element itself. Cleansing agents or antiseptic compounds can be applied to remove oil or other interfering agents from the tissue surface and reduce the effects thereof.

In one embodiment, the direction and rate of change of the concentration of glucose in the tissue 10 is determined by first monitoring the light intensity received by the output sensor 26. The monitored intensity and a calibration model are utilized by a multivariate algorithm to predict the direction and rate of change of the glucose concentration in the tissue 10. The calibration model empirically relates the known glucose concentrations in the calibration samples to the measured intensity variations obtained from said calibration samples. In a preferred embodiment, the multivariate algorithm used is the partial least squares method, although other multivariate techniques can be employed.

There is differing absorption at several wavelengths of the infrared energy as a function of the composition of the sample. The differing absorption causes intensity variations of the infrared energy passing through the analyte containing samples. The derived intensity variations of the infrared energy are received by reflectance or transmittance through the analyte-containing sample by the output element of the sensor, which is also coupled to the blood or analyte-containing sample.

The spectrum analyzer 30 of the present invention, in several embodiments, includes a frequency dispersion device and photodiode array detectors in conjunction with a computer to compare the data received from such devices to the model discussed above. Other embodiments can employ other spectroscopic technologies, for example, a scanning Fabry-Perot interferometer can be used in conjunction with a microcontroller. While a photodiode array would enable parallel analysis of several frequency bands of incident light intensity, some scanning interferometers provide a serial analysis. Other arrays, for example, an array of bolometers, can be used in conjunction with a frequency dispersion device. In some embodiments, the means of spectroscopic measurement can determined by the input light used to irradiate the tissue area to optimize the efficiency of a system.

The types and configurations of the photodiode elements can be selected from the wide variety known in the art. The frequency dispersion device and photodiode array detectors are arranged so that the array includes multiple output leads, one of which is assigned to a particular wavelength or narrow range of wavelengths of the energy source 16. The photodiode elements can provide an output voltage, current, or impedance, for example. In some embodiments, it will be necessary to provide some means of amplifying the output signal of each photodiode to reach a level where computational analysis can take place. In other embodiments, the photodiode itself can be chosen to provide a relatively large signal without external amplification; for example, an avalanche photodiode can be chosen.

In embodiments using a photodiode array, the outputs of the array can be coupled to a microcomputer, microcontroller, or other data-analyzing device that can perform multivariate analysis based on a calibration model prepared beforehand. The techniques of these models are known to statisticians. Preferably, the computation is made by the partial least squares technique as disclosed by Robinson et al. in U.S. Pat. No. 4,975,581, incorporated herein by reference.

It is has been found that considerable improvement in detection precision is obtained by simultaneously utilizing at least several wavelengths from the entire spectral frequency range of the energy source 16 to derive data for a multivariate analysis. The multivariate method allows both detection and compensation for interferences, the detection of meaningless results, as well as for modeling many types of non-linearities. Since the calibration samples used to derive the models have been analyzed on a multivariate basis, the presence of extraneous biological materials in the analyte containing tissue 10 does not prevent or distort the analysis. The model, in most applications, will have been prepared for the individual either by testing of the individual's characteristics or by characterizing the individual into a subpopulation sharing similar characteristics for which a single model can be applied. Thus, in preferred embodiments, most individual variations in the spectra will be accounted for in the calibration model.

The results of these calculations can be displayed to the user by an alphanumeric display. In some embodiments, the calculation results can be recorded for later access by a doctor or nurse, for example, to create a history of the individual's health. In other embodiments, the results can be transmitted or otherwise transferred to a separate database. In another embodiment, the results can be analyzed to determine whether the individual is approaching a dangerous situation, for example, where the glucose concentration level is determined to be dropping precipitously, and a signal indicating imminent emergency can be transmitted.

There are several avenues by which to generate estimates of analyte direction of change. One method involves generating an analyte prediction as a function of time and then estimate the rate (and/or) direction of time from these time-resolved values. The analyte predictions can be generated using the NIR spectra and some multivariate prediction technique (such as Partial Least Squares). The rate of change can be estimated for example by fitting a first-order polynomial of the glucose estimations to time. The slope of this line is equal to the rate of change.

Another method involves estimating the rate of change or direction of change from a difference spectrum. Here, a difference spectrum is a NIR spectrum generated at time t0 subtracted from a NIR spectrum generated at time t1, where t0<t1. Changes in analyte concentration over the time period dt=t1−t0 will be present in the difference spectrum.

Another method involves estimating the rate of change or direction of change directly from a single spectrum. This technique requires that some spectral signature (besides glucose absorption) be sensitive and specific to glucose change. For example, a sharp increase in glucose with time in the tissue capillaries will cause an osmotic gradient and force water from the interstitial space into the vascular space.

In any case, the methods generally require a relationship to be established between NIR spectra and some scalar reference values (analyte level, rate of change or direction of change). This process is called multivariate regression, or multivariate calibration. It requires a calibration (also called training) set of data (spectra and reference values) to be collected and used to build the calibration. The method by which the calibration data is collected is important to the accuracy and robustness of the calibration model.

The calibration data should be collected to satisfy a number of conditions. The calibration data should match the prediction data in character. That is, it should be collected using the same protocol and under the same conditions as the user would collect a spectrum. For example, if direction if change is to be determined from a single 5 minute spectrum, then the calibration data should also be a single 5 minute spectrum. This ensures that the calibration spectral variance and covariance used in the multivariate calibration step are matched to the user data. The calibration reference value range should be larger than the expected range for the user data. For example, typical rate of change values are normally distributed with a mean value near 0 mg/dL/min and standard deviation of 0.8 mg/dL/min. The calibration data should span at least +/−1 standard deviation. The calibration data should span the expected range of physiological variation caused by such parameters as user age, gender, ethnicity, diabetes type and body mass index. The calibration design should minimize unwanted correlations between the reference values and other parameters. For example, there should be no correlation between direction of change (increasing or decreasing) and measurement time of day to avoid a spurious correlation of direction of change with diurnal variation in tissue hydration state.

New characteristics and advantages of the invention covered by this document have been set forth in the foregoing description. It will be understood, however, that this disclosure is, in many respects, only illustrative. Changes can be made in details, particularly in matters of shape, size, and arrangement of parts, without exceeding the scope of the invention. The scope of the invention is, of course, defined in the language in which the appended claims are expressed.

What is claimed is:

1. An apparatus for non-invasive determination of a characteristic of change in an analyte property in tissue, comprising:
   a. radiation means for irradiating the tissue;
   b. measurement means for measuring a signal from the tissue to acquire a first output signal at a first time, and, after a first time interval, measuring a signal from the tissue to acquire a second output signal; and
   c. determination means for determining a characteristic of change of the analyte property in the tissue from the first and second output signals; wherein the determination means are further configured to:
   d. determine a set of acceptable combinations of present analyte concentration, direction of change, and rate of change of analyte concentration;
   e. determine whether the present analyte concentration, direction of change, and rate of change are within the set of acceptable combinations; and
   f. generate a signal indicative of whether the present analyte concentration, direction of change, and rate of change are within the set of acceptable combinations.

2. An apparatus according to claim 1, wherein the property is the analyte's concentration.

3. An apparatus according to claim 1, wherein the characteristic comprises the rate of change, the direction of change, or a combination thereof.

4. An apparatus according to claim 1, wherein the analyte is glucose.

5. An apparatus according to claim 1, wherein the analyte is urea.

6. An apparatus according to claim 1, wherein the analyte is alcohol.

7. An apparatus according to claim 1, wherein the analyte is a controlled substance.

8. An apparatus according to claim 1, wherein determining a characteristic of change in an analyte property comprises determining a characteristic of change in more than one analyte.

9. An apparatus according to claim 1, wherein the tissue comprises interstitial fluid.

10. An apparatus according to claim 1, wherein the tissue comprises blood.

11. An apparatus according to claim 1, further comprising means for increasing the change in the analyte property.

12. An apparatus according to claim 1, wherein the radiation means comprises means for providing light incident on a first side of the tissue and the measurement means comprises means for receiving light exiting the tissue on a second side of the tissue.

13. An apparatus according to claim 1, wherein the radiation means comprises means for providing light incident on a first side of the tissue and the measurement means comprises means for receiving light exiting the tissue on the first side of the tissue.

14. An apparatus according to claim 1, wherein the measurement means further comprises means for, after a second time interval, measuring a signal from the tissue to acquire a third output signal, and wherein the determination means comprises means for determining a characteristic of change of the analyte property from the first, second, and third output signals.

15. An apparatus for determining a direction and rate of change in concentration of an analyte in tissue comprising:
  a. energy means for providing optical energy;
  b. input means coupling the optical energy into a tissue sample;
  c. output means for capturing an optical signal from the tissue sample; and
  d. analyzing means for analyzing the optical signal and determining the direction and rate of change in concentration of the analyte, wherein the analyzing means are further configured to:
  e. determine a set of acceptable combinations of present analyte concentration, direction of change, and rate of change of analyte concentration;
  f. determine whether the present analyte concentration, direction of change, and rate of change are within the set of acceptable combinations; and
  g. generate a signal indicative of whether the present analyte concentration, direction of change, and rate of change are within the set of acceptable combinations.

16. The apparatus of claim 15, wherein the output means is configured to modulate the optical signal to enable the analyzing means to analyze a first sample of the optical signal at a first time and a second sample of the optical signal at a second time.

17. The apparatus of claim 15, wherein the analyzing means includes differentiation means for performing the mathematical function of differentiation upon at least one selected frequency of the optical signal over time.

18. An apparatus for measuring changes in concentration of an analyte disposed in tissue comprising:
  a. an excitation system configured to irradiate the tissue;
  b. a collection system configured to capture radiation at a plurality of selected frequencies emanating from the tissue at a first time and a second time; and
  c. an analysis system configured to determine the direction or rate of change, or both, of the concentration of the analyte from the captured radiation, wherein the analysis system is further configured to:
  d. determine a set of acceptable combinations of present analyte concentration, direction of change, and rate of change of analyte concentration;
  e. determine whether the present analyte concentration, direction of change, and rate of change are within the set of acceptable combinations, and
  f. generate a signal indicative of whether the present analyte concentration, direction of change, and rate of change are within the set of acceptable combinations.

19. An apparatus according to claim 18, further including an acceleration system configured to accelerate changes in concentration of the analyte in the tissue during the interval between the first and second times.

* * * * *